United States Patent
Nordmann et al.

(10) Patent No.: US 10,745,733 B2
(45) Date of Patent: Aug. 18, 2020

(54) KIT AND METHODS FOR THE RAPID DETECTION OF THE ABSENCE OR PRESENCE OF A β-LACTAMASE IN SAMPLES OF BODY FLUIDS

(71) Applicant: UNIVERSITE DE FRIBOURG, Fribourg (CH)

(72) Inventors: Patrice Nordmann, Fribourg (CH); Laurent Poirel, Fribourg (CH); Nicolas Kieffer, Fribourg (CH)

(73) Assignee: UNIVERSITE DE FRIBOURG, Fribourg (CH)

( * ) Notice: Subject to any disclaimer, the term of this patent is extended or adjusted under 35 U.S.C. 154(b) by 7 days.

(21) Appl. No.: 15/763,226

(22) PCT Filed: Oct. 7, 2016

(86) PCT No.: PCT/EP2016/074001
§ 371 (c)(1),
(2) Date: Mar. 26, 2018

(87) PCT Pub. No.: WO2017/060427
PCT Pub. Date: Apr. 13, 2017

(65) Prior Publication Data
US 2018/0282778 A1 Oct. 4, 2018

(30) Foreign Application Priority Data

Oct. 9, 2015 (EP) ..................................... 15189246

(51) Int. Cl.
*C12Q 1/04* (2006.01)
*C12Q 1/34* (2006.01)

(52) U.S. Cl.
CPC ................. *C12Q 1/04* (2013.01); *C12Q 1/34* (2013.01)

(58) Field of Classification Search
CPC ....................................................... C12Q 1/34
See application file for complete search history.

(56) References Cited

U.S. PATENT DOCUMENTS

2004/0253624 A1 12/2004 Smith et al.
2007/0003997 A1 1/2007 Kemmochi et al.

FOREIGN PATENT DOCUMENTS

| EP | 2260943 A1 | 12/2010 |
|---|---|---|
| WO | 2005/071096 A2 | 8/2005 |
| WO | 2012/162133 A1 | 11/2012 |
| WO | 2012/175637 A1 | 12/2012 |
| WO | 2013/049648 A1 | 4/2013 |
| WO | 2013/072494 A1 | 5/2013 |

*Primary Examiner* — Bin Shen
(74) *Attorney, Agent, or Firm* — Robert C. Netter, Jr.; Dann, Dorfman, Herrell & Skillman (57) ABSTRACT

The present invention concerns a kit and methods for the detection of absence or presence of a β-lactamase, for example a penicillinase, in a sample comprising or derived from a body fluid taken from a patient suffering from an infection. In some embodiments, the goal of the invention is to rapidly identify infections which can be treated effectively with a penicillin compound. The invention contributes to slowing down the occurrence of resistances to last generation antibiotics. This is achieved by using penicillin compounds for treating infections whenever this can be done efficiently. In brief, the present invention provides a tool for maximizing the use and efficiency of penicillin antibiotics. In other embodiments, the test kit of the invention can be used to detect cephalosporinases (including ESBLs) or carbapenemases.

6 Claims, 4 Drawing Sheets

KIT AND METHODS FOR THE RAPID DETECTION OF THE ABSENCE OR PRESENCE OF A β-LACTAMASE IN SAMPLES OF BODY FLUIDS

The present application is § 371 application of PCT/EP2016/074001, filed Oct. 7, 2016, which claims priority to EP Application No. 15189246.0, filed Oct. 9, 2015. The entire disclosure of each of the foregoing applications is incorporated by reference herein.

TECHNICAL FIELD

The present invention relates to kits and methods for the detection of absence or presence of β-lactamase, such as a penicillinase, cephalosporinase or carbapenemase, in a body fluid, to a method for identifying infections treatable with a penicillin compound, and to the use of a filter system for detection of absence or presence of β-lactamase in a body fluid.

BACKGROUND ART AND THE SOLUTION APPROACH OF THE INVENTION

Multidrug resistance is now emerging at an alarming rate worldwide. The rise of antibiotic-resistant bacterial strains represents a serious threat to public health and the economy. The severity of this menace is amplified by the fact that research for new antibiotic agents is currently stalled. It may be possible that no new agent active against multidrug resistant bacteria will be put on the market in a close future. The 20$^{th}$ century was the "century of antibiotics", marked by the discovery and the continuous development of new more and more active antibiotics, but no new antibiotic family has been available for clinicians since 1987. In a world with few effective antibiotics, modern medical advances such as intensive care, transplant and chemotherapy (cancer treatment) may no longer be possible due to the threat of untreatable infections.

Most of the public bodies such as the World Health Organization (2014), the UK Government (2014), the Center for Disease Control and Prevention in the USA (2013) and the Davos Economic Forum in Switzerland (since 2013) have pull the alarm signal to try to control this complex health issue. It is estimated that 25,000 patients die each year in Europe due to multidrug resistance.

As underlined by the latest and important report from the White House in the US (September 2014, National Strategy for Combating Antibiotic Resistant Bacteria) a multiple facet approach is needed. Basically, this strategy is intended to reach four synergistic goals (i) antibiotic stewardship from agriculture to human medicine, (ii) surveying emerged and emerging resistance determinants (iii) accelerate basic and applied research and the development for new antibiotics, other therapeutics and vaccines, (iv) and advance development and use of rapid and innovative diagnostic tests for identification and characterization of resistant bacteria.

Infections are mostly due to either Gram positives such as *Staphyloccus aureus* and Gram negatives such as *Escherichia coli*. Most of the important resistance issues are now in emerging Gram negatives (lack of novel anti-Gram negatives agents). They are the main causes of infections in humans. They are the source of both community-acquired and hospital-acquired infections (urinary tract infections, septicemia, intra-abdominal infections . . . ). By far, clinically-significant Gram negatives are the Enterobacteriaceae (*E. coli, Klebsiella pneumoniae, Salmonella* . . . ).

Urinary tract infections (UTIs) are the most prevalent bacteria-related infectious diseases in humans, with an estimated overall incidence of 18/1,000 persons per year in the United State. According to the Centers for Disease Control and Prevention, UTIs that are mostly due to *Escherichia coli* (75%) account for more than 8.6 million visits to health care professionals each year in the United States. In addition, multidrug resistance is now emerging worldwide among Gram-negative organisms, which are mostly responsible for UTIs.

A very common resistance trait in Gram-negative bacteria is associated to resistance at least to amino-penicillins due the production of narrow- to broad-spectrum-ß-lactamases. Those enzymes hydrolyze at least aminopenicillins. Resistance to aminopenicillins is observed in 40-80% of *E. coli* isolates worldwide depending of the geographic area The ß-lactamases are commonly classified according to two different general schemes; the Ambler molecular classification and the Bush-Jacoby-Medeiros functional classification. The Ambler scheme classifies ß-lactamases into four classes according to the protein homology of enzymes, ß-lactamases of class A, C and D are serine-ß-lactamases and class B enzymes are metallo ß-lactamases. The second classification is the Bush-Jacoby-Medeiros functional scheme based on functional properties of the enzymes. The term "extended-spectrum ß-lactamases" (ESBLs) was originally applied to the TEM and SHV derivatives that can hydrolyze oxyiminocephalosporins being classified in the group 2be with the Bush-Jacoby-Medeiros functional schemes in the 1980's. Those enzymes belong to the Ambler class A group of ß-lactamases and their activity is inhibited by class A inhibitors such as tazobactam, clavulanic acid and sulbactam. More than 700 distinct ß-lactamases have been described, many of them hydrolyzing extended-spectrum cephalosporins and belonging to different types of Ambler groups of enzymes. All ß-lactamases hydrolyze at least amino-penicillins such as amoxicillin.

Resistance to aminopenicillins in Enterobacteriaceae is mostly due to naturally produced narrow-spectrum ß-lactamases such as SHV enzymes in *K. pneumoniae* or AmpC enzymes in *Enterobacter* sp, *Serratia* sp. or to acquired narrow-spectrum class A or class D enzymes such as TEM-1, TEM-2, SHV-1 or OXA-1 enzymes.

One of the most important emerging resistance traits corresponds to resistance to broad-spectrum β-lactams in Enterobacteriaceae, that is mainly associated with extended-spectrum ß-lactamases, i.e ESBLs are of the CTX-M type. It is observed in 5 to 80% of *E. coli* isolates worldwide. Hence, ESBL-E are usually resistant to most β-lactams including amoxicillin, cefotxime, ceftazidime, except cefoxitin and carbapenems. Therefore, efficient treatment of those infections is becoming challenging due to a concomitant and rapid increase of the prevalence rate of ESBL-E worldwide and the perspective of a paucity of novel anti-Gram-negative molecules. Use of a rapid detection technique to evidence aminopenicillin susceptibility or resistance may significantly contribute to save the efficacy of more broad-spectrum antibiotics of the ß-lactam family as well as other antibiotic families such as fluoroquinolones and aminoglycosides for treating in particularly those infections due to ESBL producers.

WO 2013/072494 discloses a method for detecting the presence of expanded spectrum β-lactamase (ESBLs) producing bacteria in a sample. While this test is useful for specifically detecting the presence of ESBL activity, it does not allow determining whether an infected patient can be successfully treated with an aminopenicillin. As indicated above, 20-60% of *E. coli* isolates are not resistant to aminopenicillins. In order to reduce the non-adequate or irresponsible use of broad-spectrum antibiotics, it would be advantageous to treat infections due to penicillin-sensitive bacteria with a narrow spectrum penicillin.

It is thus a goal of the invention to reduce the occurrence of resistance to the few broad-spectrum antibiotics that are currently still effective to treat infections due to ESBL producers. This objective is addressed by designing a technique for rapid identification of susceptibility or resistance to aminopenicillins directly from urines or from blood cultures.

The invention is a support for prescription of narrow-spectrum penicillins to treat of UTIs and blood infections due to bacteria that do not possess a narrow or a broad-spectrum-ß-lactamase.

It is in particular a more global goal of the invention to treat UTIs and other infections with penicillins whenever this is possible, such as in the case of those 20-60% of *E. coli* UTIs, which are not characterized by resistance to penicillins, such as aminopenicillins.

The result of the approach of the invention would be that the use of the currently very few effective broad-spectrum antibiotics is reduced and, as a consequence, the efficacy of those antibiotics can be maintained.

The invention is in particular based also on the notion that the non-adequate or irresponsible use of antibiotics is a key factor for the emergence of resistance to antibiotics. The invention addresses this problem by providing a possibility of using penicillins in the treatment of UTIs and other infections whenever a positive treatment outcome can be anticipated.

The present invention addresses the problems depicted above.

SUMMARY OF THE INVENTION

The present inventors provide a new kit and methods for the rapid detection of the occurrence of a β-lactamase, in particular a penicillinase, in a sample comprising or derived from a body fluid. The kit requires readily available and affordable components and can therefore be realized at low cost. Furthermore, the kit is rapid, allowing the possibility of treatment with a narrow-spectrum antibiotic within a few hours or possibly less.

In summary, the kits and methods of the invention are important tools for limiting the use of last generation antibiotics and last resort treatments. In so doing, the invention contributes to slowing down the occurrence of resistances to last generation antibiotics. In some aspects, the invention contributes to limiting the use of antibiotics used to treat infections with extended spectrum β-lactamase producing bacteria, in cases where the use of such antibiotic is not necessary.

Thanks to the kits and methods of the invention, the use and utility of first generation penicillin antibiotics may be maximized by providing rapid information with respect to the efficacy of such first generation penicillin antibiotic in the treatment of a particular infection, in some embodiments of the invention.

In an aspect, the invention provides a kit for the detection of absence or presence of β-lactamase in a sample comprising or derived from a body fluid taken from a patient suffering from an infection, the kit comprising: (1) a filter system comprising a recipient comprising a filter at or in vicinity of the bottom of the recipient, wherein the filter is adapted to receive said sample and to retain bacteria and/or bacterial proteins contained in the sample, wherein said filter system is adapted to centrifugation; (2) a surfactant solution; and (3) an indicator solution comprising a β-lactam compound and a colour indicator.

In an aspect, the invention provides a kit for the detection of absence or presence of a β-lactamase, in particular a penicillinase, in a urine sample taken from a patient suffering from a urinary tract infection, the kit comprising: (1) a filter system comprising a recipient comprising a filter; (2) a surfactant solution comprising a surfactant; and (3) an indicator solution comprising at least one β-lactam compound and a color indicator. Preferably, the β-lactam compound is at least one penicillin compound.

In another aspect, the invention provides a kit for the detection of absence or presence of a resistance to an antibiotic in a sample comprising or derived from body fluid taken from a patient suffering from an infection, the kit comprising: (1) a filter system comprising a recipient comprising a filter; (2) a surfactant solution comprising a surfactant; and (3) an indicator solution comprising at least one antibiotic compound and a color indicator. The kit according to this aspect may be used to detect the presence of resistance to any particular antibiotic for which a rapid detection may be desired.

In an aspect, the invention provides a method for detecting the presence of a β-lactamase in a sample comprising or obtained from a body fluid taken from a patient suffering from an infection, the method comprising the steps of: loading the sample onto a recipient comprising a filter at or in vicinity of the bottom of the recipient, wherein the filter is adapted to receive said sample and to retain bacteria and/or bacterial proteins contained in the sample, wherein said filter system is adapted to centrifugation; exposing filtered bacteria in said recipient to a surfactant solution; exposing bacterial proteins in said recipient to an indicator solution comprising a color indicator and a β-lactam compound; and, determining the presence or absence of a β-lactamase from the color of the indicator solution after incubation.

In an aspect, the invention provides method for detecting the presence of any β-lactamase in a sample, the method comprising the steps of: loading a sample onto a recipient comprising a filter; exposing bacteria to a surfactant solution; exposing bacterial proteins to an indicator solution comprising a penicillin compound; and, determining the presence or absence of a β-lactamase, in particular penicillinase, from the color of the indicator solution after incubation.

In an aspect, the invention provides method for detecting the presence of any β-lactamase in a urine sample, the method comprising the steps of: loading a urine sample onto a recipient comprising a filter; exposing filtered bacteria to a surfactant solution; exposing bacterial proteins to an indicator solution comprising a penicillin compound; and, determining the presence or absence of a β-lactamase, in particular penicillinase, from the color of the indicator solution after incubation.

In an aspect, the invention provides a method for identifying infections treatable with a penicillin compound, the method comprising the steps of: loading a sample onto a recipient comprising a filter; exposing filtered bacteria to a surfactant solution; exposing lysed and filtered bacteria to an indicator solution and a penicillin compound; and, determining the presence or absence of a β-lactamase, in particular a penicillinase, from the color of the indicator solution after incubation.

In an aspect, the invention provides a method for detecting the presence of a β-lactamase, in a sample of a patient suffering from an infection, the method comprising steps defined herein above.

In an aspect, the invention provides a method for identifying infections treatable with a penicillin compound.

In an aspect, the invention provides the use of a kit for identifying infections treatable with a β-lactam compound.

In an aspect, the invention provides the use of a kit for identifying infections treatable with a penicillin compound.

In an aspect, the invention provides a method for detecting, in a sample comprising or derived from a body fluid, the occurrence of any one or more selected from the group of (i) antibiotic resistances, (i) the presence of a β-lactamase, in particular a penicillinase, and (iii) infections treatable with a penicillin compound. The invention provides the use of the kit of the invention in such methods.

In an aspect, the invention provides a method for detecting, in a sample comprising or derived from a body fluid, the occurrence of penicillinase and/or resistance to a penicillin compound.

In an aspect, the invention provides a method for detecting, in a sample comprising or derived from a body fluid, the occurrence of cephalosporinase and/or resistance to a cephalosporin compound.

In an aspect, the invention provides a method for detecting, in a sample comprising or derived from a body fluid, the occurrence of a carbapenemase and/or resistance to a carbapenem compound.

In an aspect, the invention provides a method and kit for reducing the use of broad-spectrum antibiotics and/or last resort antibiotics such as fluoroquinolones or other broad spectrum antibiotics in the treatment of infections. This method preferably comprises the steps of the method of the invention.

In an aspect, the invention provides a method and kit for reducing the occurrence of resistance to antibiotics, by identifying infections treatable with a penicillin compound.

The infection is preferably selected from urinary tract infections and bloodstream infections such as bacteremia and septicemia. The sample is preferably a urine sample, a blood sample or derived from a blood sample, for example blood culture sample.

Further aspects and preferred embodiments of the invention are defined herein below and in the appended claims. Further features and advantages of the invention will become apparent to the skilled person from the description of the preferred embodiments given below.

BRIEF DESCRIPTION OF THE DRAWINGS

FIGS. 3 A and 3 B are photographs taken at successive stages of the test protocol in accordance with an embodiment of the method of the present invention.

DETAILED DESCRIPTION OF THE PREFERRED EMBODIMENTS

For the purpose of the present specification, the expression "comprising" and its various grammatical forms is intended to mean "includes, amongst other". It is not intended to mean "consisting only of".

In some embodiments, the kit and methods of the present invention aim at detecting the presence or absence of a β-lactamase in a urine sample taken from a patient suffering from a urinary tract infection. In some embodiments, the kits and methods aim at detecting the presence or absence of any type of β-lactamase.

In some embodiments, the kit and methods of the present invention aim at detecting the presence or absence of a β-lactamase in a blood or serum sample taken from a patient suffering from an infection, such as bacteremia, septicemia and/or blood infection. In some embodiments, the kits and methods aim at detecting the presence or absence of any type of β-lactamase. For example, a sample of a blood culture may be used for the purpose of the present invention.

For the purpose of the present invention, the expression "a sample derived from a body fluid" encompasses a sample of a blood culture, which is obtained by inoculating a medium with a blood or serum sample and cultivating the medium such as to promote the growth and thus increase the number and/or concentration of bacteria present in the blood sample.

In a preferred embodiment, said sample comprising or derived from a body fluid is a urine sample or a sample of a blood culture, in particular a positive blood culture.

In a preferred embodiment, the kits and methods aim at detecting the presence or absence of one or more selected from the group consisting of: (i) penicillinase, (ii) cephalosporinase (iii) extended spectrum β-lactamase, and (iv) carbapenemase. In a most preferred embodiment, the kits and methods aim at detecting the presence (or absence) of any one of these four types of β-lactamases (i)-(iv).

It is noted that, for example, the cephalosporinase (ii) also hydrolyzes penicillins, such as amino-penicillins, however, a cephalosporinase does not hydrolyze a carbapenem antibiotic. In some preferred embodiment, it is an objective of the invention to detect the presence of any type of β-lactamase activity. Therefore, in an embodiment, the goal of the kits and methods of the invention is not to distinguish between the β-lactamases (i)-(iv) nor to identify the presence of any one of them in particular. In accordance with this embodiment, the main goal is to identify, yes or no, whether any one of those four is present in the sample. It is noted that all of the β-lactamases (i)-(iv) generally hydrolyze penicillin compounds, in particular aminopenicillins, such as amoxicillin. Therefore, one may also say that, in an embodiment, the kits and methods of the invention aim at detecting the presence or absence of a penicillinase. In a preferred embodiment, the penicillinase to be detected is an aminopenicillinase, that is, any enzyme capable of degrading an aminopenicillin.

In some alternative or other embodiments, the kits and methods of the invention concern the detection of a cephalosporinase, preferably an extended-spectrum cephalosporinase (ESBL) or the detection of a carbapenemases. In accordance with these embodiments, it is an objective of the invention is to detect the presence of a particular type or groups of β-lactamase, such as cephalosporinase or carbapenemases activity.

In some embodiments, the kits and methods of the invention comprise a filter system. The filter system comprises a recipient and a filter. The filter is generally at or in vicinity of the bottom of the recipient. Preferably, the recipient has a bottom opening, wherein said filter closes and/or delimits said bottom opening, such that a sample contained in the recipient may exit the recipient through said bottom opening by being filtered through said filter. The recipient is preferably adapted to receive a sample, in particular a urine sample. The filter of the filter system is preferably adapted to retain bacteria contained in the sample and/or to retain bacterial proteins, such as β-lactamase, that are contained in the bacteria that are present in the sample, for example the urine sample or the blood culture. The bottom of the recipient may be equipped to discard the filtered urine or blood culture (filtrate), for example a draining tube or a filtrate collector recipient.

Preferably, the kit of the invention comprises or may be used with a tube adapted to centrifugation, said tube being adapted to receive said filter system and to collect a filtrate from said filter system during centrifugation.

In some embodiments, the filter system of the invention is a centrifuge tube filter system. Preferably, the centrifuge tube filter system comprises a filter cup comprising a filter and a centrifuge tube for harboring said filter cup. The "filter cup" is preferably an inner tube, which can be placed inside the centrifuge tube. The bottom of the inner tube comprises or consists of a filter, which preferably comprises a membrane. The centrifuge filter system preferably further comprises a centrifuge tube for harboring said filter cup. The centrifuge tube generally comprises a bottom part which is empty, the filter cup being retained in the upper part of the centrifuge tube. The bottom part of the centrifuge tube is closed and waterproof and functions as filtrate collector recipient. If a sample is placed in the filter cup, centrifugation results in the filtering of water and some of the dissolved components comprised in the sample across the filter and being retained in the lower part of the centrifuge tube. Larger molecules, such as proteins other polymers are generally retained by the filter. Centrifuge tube filter systems are commonly used in laboratory, for example for DNA extraction.

The filter of the centrifuge filter system is preferably selected so as to be capable of retaining bacteria during centrifugation for eliminating liquid parts, in particular water, of the sample.

Furthermore, the filter is preferably selected so as to retain bacterial proteins during centrifugation of a sample containing destroyed bacteria. For example, a 0.45 μm filter may be used.

Figure 1:
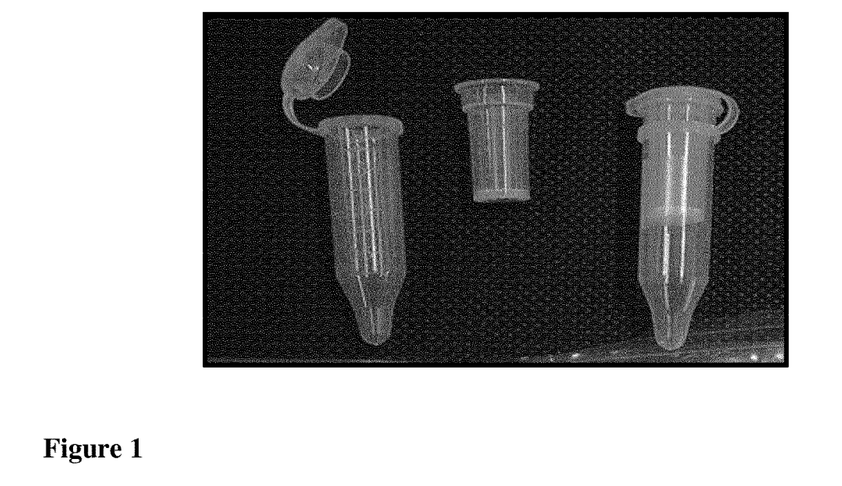
FIG. 1 shows an exemplary filter tube system that can be used for carrying out the method of the invention and which may be part of the kit in accordance with an embodiment of the invention.

FIG. 1 is a photograph showing the elements of the Spin-X centrifuge tube filter system which may be used for the purpose of the present invention. This centrifuge tube filter system is commercially available under the tradename Costar®. On the left side of the photograph, the centrifuge tube is seen and the filter cup is shown in the middle. On the right side the photograph shows the assembled centrifuge tube filter system, in which the filter cup has been placed inside the centrifuge tube and is retained in the upper part of the latter.

In an alternative embodiment, the filter system is not a system that is adapted for centrifugation.

For example, the filter system may comprise a filter comprising a membrane, which retains bacteria and/or bacterial proteins, and lets pass water and some comparatively small dissolved molecules without the need of centrifugation. In such a system, water may pass the filter under the effect of gravity alone.

In some embodiments, the kit and methods of the present invention comprise a surfactant solution comprising a surfactant. The purpose of the surfactant solution is to destroy the bacteria contained in the sample while keeping the proteins and enzymes active, in particular β-lactamases, if present in the bacteria. The concentration of the surfactant is thus chosen so as to efficiently destroy bacteria, in particular Gram negative bacteria. For example, buffer B-PER II in water may be used as a surfactant solution.

In some embodiments, the kit and methods of the present invention comprise an indicator solution. In an embodiment, the indicator solution comprises at least one antibiotic compound and a color indicator. In a preferred embodiment, the indicator solution comprises at least one penicillin compound and a color indicator.

In principle, the present invention is not limited to any particular color indicator. Preferably, the color indicator is a chemical compound. In an embodiment, the color indicator is susceptible of detecting a pH change. In other words, the color indicator is preferably a halochromic chemical compound. Accordingly, the color of the color indicator is dependent on the pH of the solution.

If a sample comprises a β-lactamase, the latter will metabolize the β-lactam compound added to the sample by opening the ß-lactam ring, which results in the production of an acidic ß-lactam molecule. The resulting change in pH can be detected by way of the color indicator.

In an embodiment, the color indicator is phenol red. The color of phenol red exhibits a gradual transition from yellow to red over the pH range 6.8 to 8.2. In other words, the concomitant presence of a β-lactamase and a penicillin compound in the sample will result in a color change from red to yellow.

In an alternative embodiment, the color indicator and the β-lactam compound are the same chemical molecule. In this case, the β-lactam compound is preferably a chromogenic compound, which changes color when being metabolized by a β-lactamase.

In this case, the activity of the β-lactamase directly chemically degrades the color indicator, and the latter changes color as a result of the structural change in the molecule due to the enzymatic degradation. In this case, the color indicator does not necessarily need to change color in dependence of pH. An example of a chromogenic antibiotic is chromogenic cephalosporin HMRZ-86, disclosed by Hanaki H. et al, in J. Antimicrob. Chemother. (2004) 53 (5): 888-889.

In an embodiment of the kits and methods of the invention, the indicator solution comprises β-lactam compound.

In an embodiment of the kits and methods of the invention, the β-lactam compound is a penicillin compound. The penicillin compound is preferably selected from the group consisting of aminopenicillins including acylaminopenicillins, natural penicillins, carboxypenicillins and ureidopenicillins.

In an embodiment of the kits and methods of the invention, the penicillin compound is selected from the group consisting of: amoxicillin, penicillin G, penicillin P, penicillin V, ampicillin, pivampicillin, hetacillin, bacampicillin, metampicillin, talampicillin, and epicillin.

In a preferred embodiment, the penicillin compound is an aminopenicillin, preferably amoxicillin.

The penicillin compound may be provided in a deprotonated form and in the form of a salt of the protonated form, as well as esterified or alkylated forms of the penicillin compound.

In a preferred embodiment, the penicillin compound is a compound having the structure of formula (I) below:

including esters of the compound of formula (I) (such as in pivampicilin, bacampicillin, talampicillin, etc), deprotonated forms of the compound of formula (I) and salts of said deprotonated forms;
wherein R is a substituent comprising, for example, from 1-20 carbons and 0 to 5 heteroatoms, preferably 3-15 carbons and 0-4 heteroatoms, most preferably, 6-10 carbons and 0-3 heteroatoms, and wherein R may form a ring connected to the nitrogen of —NH— in formula (I), in which case H in NH is of formula (I) absent (such as in hetacillin, for example).

In another embodiment, the β-lactam compound is not a penicillin compound as defined above. In such embodiments, the kits and methods of the invention are preferably used for the detection of extended-spectrum cephalosporinase (ESBL) or carbapenemases. In accordance with such embodiments, the β-lactam compound is preferably a cephalosporin compound or a carbapenem compound.

In an embodiment, the β-lactam compound is selected from cephalosporins, such as cepcefotaxime, cefepime, ceftriaxone, ceftazidime, ceftpirome and aztreonam; and from carbapenems, such as imipenem, meropenem, ertapenem, doripenem, and panipenem.

In an embodiment of the invention, the β-lactam compound is selected from penicillin compounds, cephalosporin compounds and from carbapenem compounds, for example from the specific compounds disclosed in this specification.

If the sample is a blood or serum sample or a blood culture sample, the sample is preferably pretreated, and the method preferably comprises a pretreatment step. Preferably, the sample is exposed to a surfactant, optionally incubated for 0.5-60 minutes and centrifuged. The supernatant may be suspended, for example in sterile water or saline solution. The pretreatment allows removing unnecessary and undesired components present in the blood or blood culture sample, such as blood cells and metabolites or nutrients of the blood culture. The invention encompasses the use of any "treatment solution" in addition or as an alternative to said surfactant, allowing the lysis of blood cells, and/or removal of undesired components in the blood culture. The removal may, for example, be conducted by centrifugation or by filtration, as long as bacterial proteins can be separated from undesirable components that may interfere with the kit of the invention, in particular with the readout.

In accordance with an embodiment of the method of the invention, the sample is loaded on the recipient of a filter system comprising a filter, wherein the filter system may be as described elsewhere in this specification.

In an embodiment, the filter in said filter system is selected so at to retain bacterial proteins during a step of filtering.

Preferably, the method comprises the step of filtering said sample through said filter for separating bacteria from the sample. For example, if a centrifuge tube filter system is used, the sample may be directly added into the filter cup placed in the centrifuge tube. Filtering is then accomplished by centrifuging. Centrifugation is preferably conducted at a speed and/or acceleration that is sufficient to achieve the transfer of the liquid parts of the sample, for example the urine, across the filter of the filter cup.

The bacteria will be retained on the filter and have thus been separated from the sample. If the sample is a urine sample, the bacteria are separated from the urine, in particular from water of the urine and small dissolved molecules, which are not retained by the filter. The filtered sample (the filtrate) can be discarded.

If the sample initially loaded into the recipient did not contain a sufficient number of bacteria for allowing a correct test outcome, more urine may be loaded into the container, and the filtering step is conducted anew. In particular, the steps of adding a sample in said recipient and filtering the sample can be repeated several times. Preferably, the same recipient is used, and new urine is added into the recipient after filtration. In case a centrifuge tube filter system is used, the centrifuge tube containing the urine filtrate may be discarded, the filter cup containing already some bacteria on the filter is placed in a new centrifuge tube, urine of the same patient is added again into the same filter cup, and centrifugation is conducted again with the new centrifuge tube. The above may apply, for example, to urine samples.

Preferably, the method comprises the step of exposing bacteria to a surfactant solution. Preferably, the method comprises the step of exposing filtered bacteria in said recipient to a surfactant solution. For example, the method comprises adding a surfactant solution to said recipient comprising the bacteria retained on the filter. The surfactant solution has been described elsewhere in this specification. Preferably, the surfactant solution is mixed with the bacteria on the filter. This may be made, for example, by pipetting up and down, that is, sucking in and expelling the surfactant liquid added to the container into the pipet tip by pipetting. Mixing can also be performed by vortex mixing, for example.

If necessary, the composition comprising the surfactant solution and the bacteria is incubated for a time that is sufficiently long for the bacteria to be disintegrated and/or lysed. For example, incubation for 1 to 45 minutes, preferably 5 to 30 minutes, more preferably 10-25 minutes is preferred.

In an embodiment, the method of the invention comprises the step of exposing bacterial proteins to an indicator solution comprising a color indicator. The indicator solution is preferably added to surfactant-treated bacteria and/or bacterial proteins released due to surfactant treatment.

In an embodiment, the indicator solution is added after addition of the surfactant solution. The invention does not exclude the possibility that the indicator solution is added before or at the same time as the surfactant solution. For examples, in some embodiments, the kit comprises one solution which functions as surfactant as well as indicator solution.

The indicator solution is preferably as described elsewhere in this specification, in particular with respect to the kit of the invention. Basically, the indicator solution comprises a color indicator and a penicillin compound.

In an embodiment, the method of the invention comprises the step of incubating the composition comprising bacterial proteins, the surfactant solution and the indicator solution. Preferably, the recipient comprising the bacterial proteins and the indicator solution is incubated.

Incubation is preferably conducted at a temperature of 20-40° C., preferably 25-39° C. and more preferably 30-37.5° C.

Incubation is preferably conducted for 0.25-3 hours, preferably 0.5-2 hours, and most preferably 0.75-1.5 hours.

In summary, and in accordance with a preferred embodiment, the methods of the invention comprise the steps of:
(1) providing a filter system comprising a recipient comprising a filter at or in vicinity of the bottom of the recipient, wherein the filter is adapted to receive said sample and to retain bacteria and/or bacterial proteins contained in the sample, wherein said filter system is adapted to centrifugation;
(2) adding said sample in said recipient of said filter system;
(3) filtering said sample through said filter for separating bacteria and/or bacterial proteins from the sample;
(4) if not done previously, exposing bacteria to surfactant solution;
(5) adding an indicator solution comprising at least one β-lactam compound and a colour indicator into the recipient comprising bacterial proteins;
(6) incubating the recipient comprising bacterial proteins and said indicator solution; determining the presence of a β-lactamase by detecting a color change of said indicator solution, and the absence of a β-lactamase, in particular a penicillinase, by detecting an absence of a color change of said indicator solution.

Regarding step (4) in the embodiments discussed above, this step is optional and/or can be conducted separately or previously. For example, the sample and/or body fluid may be treated with the surfactant solution before the sample is added to the recipient comprising the filter.

In a preferred embodiment, step (4) comprises adding a surfactant solution to said recipient comprising bacteria.

In an embodiment, the methods of the invention comprise the steps of:
(1) providing a filter system comprising a recipient comprising a filter;
(2) adding a urine sample in said recipient comprising a filter;
(3) filtering said urine through said filter for separating bacteria from the urine;
(4) adding a surfactant solution to said recipient comprising bacteria;
(5) adding an indicator solution comprising at least one β-lactam compound and a colour indicator into the recipient comprising bacterial proteins;
(6) incubating the recipient comprising bacterial proteins and said indicator solution;
(7) determining the presence of a β-lactamase, such as penicillinase, by detecting a color change of said indicator solution, and the absence of a β-lactamase, in such as penicillinase, by detecting an absence of a color change of said indicator solution.

Figure 3:
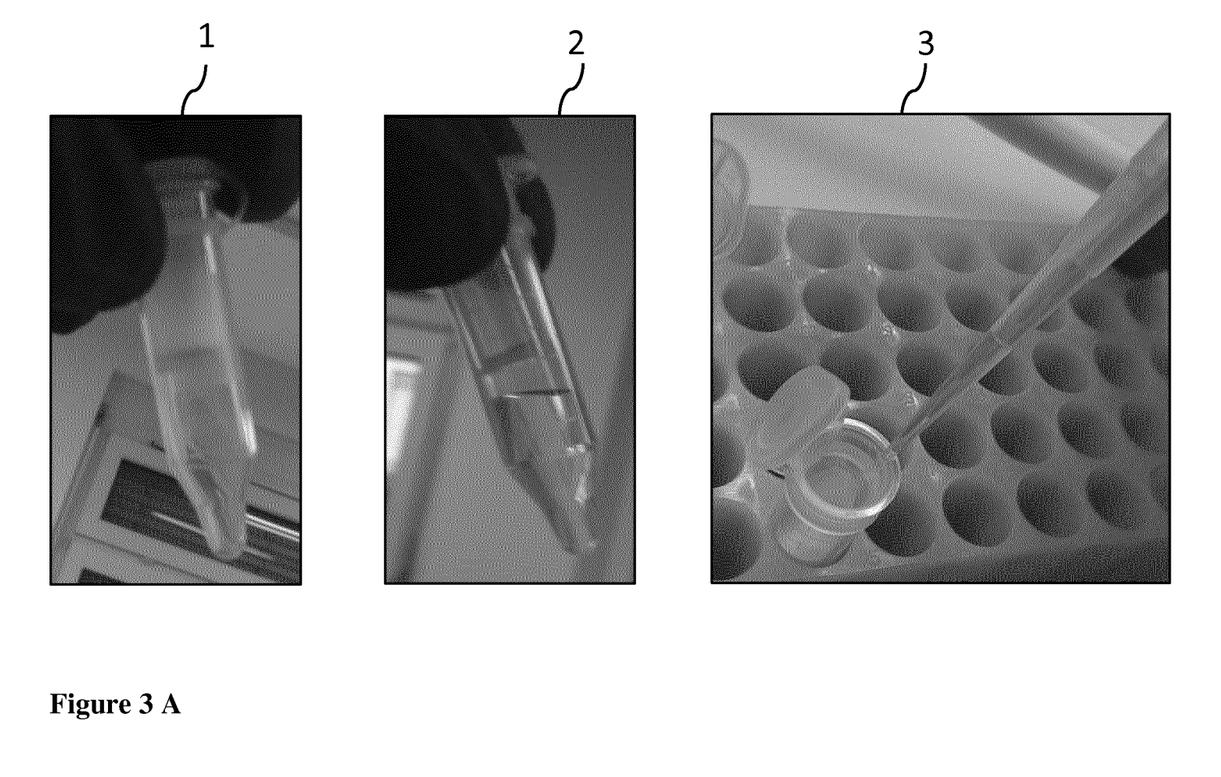

After incubation, the test result can be determined from the color of the composition containing the indicator solution and the bacterial proteins. At this stage, the solutions are preferably still in the recipient comprising the filter, for example a filter cup (FIG. 3 B nos 5 and 6). For example, if phenol red is used as color indicator, a change of color from red to yellow in the course of incubation indicated the presence of a β-lactamase. If the β-lactam compound used in the method and kit was a penicillin compound, the yellow color test outcome means that treatment with a penicillin compound, such as aminopenicillins including acylaminopenicillins, natural penicillins, carboxypenicillins and ureidopenicillins, is not possible. On the other hand, if no color change is observed in this example, the urinary tract infection is expected to be caused by a bacterium that is susceptible to the penicillin compounds cited above. Treatment with a penicillin compound as defined in this specification, in particular amoxicillin, is thus possible and should be effective.

An advantage of the method of the invention is that, thanks to the use of a filter system, it is not necessary to remove the sample, for example the urine, from the recipient comprising the bacteria. Such removal generally has to be performed manually in prior art kits. Generally, the tube or recipient containing the sample and the bacteria, for example in the form of a pellet, is opened, and sample, for example the urine or blood culture is removed by pipetting. Such a removal step is undesirable, because it involves a risk of sample spilling, contamination, the requirement of additional material, and so forth.

In accordance with the present invention, the step of removal urine or blood derived samples from a recipient comprising a pellet of bacteria or otherwise concentrated bacteria can be avoided, because sample and other liquids, such as the surfactant solution, are removed by filtering.

The kit of the invention can be used for identifying infections, for example urinary tract infections and bloodstream infections, treatable with a penicillin compound, in particular a penicillin compound as defined elsewhere in this specification.

EXAMPLES

Example 1

The goal of this example is to implement an exemplary protocol for conducting the rapid detection of the presence (or absence) of resistance to amoxicillin from a urine sample taken from patients suffering from a urinary tract infection.

Material
Amoxicillin (Sigma Aldrich).
Phenol red (Sigma Aldrich).
Centrifuge.
B-PER II (Thermoscientific, Rockford, Ill. 61105, US non-ionic detergent in 20 mM Tris, HCl, pH 7.5, product no. 78260).
Spin-X centrifuge tube with an inner tube equipped with a 0.45 mm filter (Costar®) (FIG. 1).
A thermal block.

Preparation of Solution P
Prepare a concentrated solution of red phenol (0.5% weight/volume)
  Mix 2 ml of this solution in 16.6 ml of distilled water.
  Add Amoxicillin in order to have a final concentration of 10 mg/ml.
  Adjust the pH at 6.8-7 by adding droplets of NaOH (1N) or HCl (1N).

Test Protocol
1. Put 1 ml of urine sample on a Spin-X centrifuge tube filter and centrifuge 5 minutes at 14,000 rpm. Discard the supernatant. The step may be repeated in required, 1-10 times to collect an important concentration of bacteria on the filter. The more urine is put on the tube, the longer the time for centrifugation.

Photograph 1 in FIG. 3 A shows a Spin-X centrifuge tube filter with a sample containing bacteria placed in the filter cup. Photograph 2 shows the tube after centrifugation.

2. Add 50 µl of PER-II solution on the filter (FIG. 3 A photograph 3) and vortex for 5 s.

3. Add 50 µl of the solution P on the filter (FIG. 3 B photograph 4) and incubate the tube at 37° C. in a thermal block for 1 hour of incubation.

In FIG. 3 B, photographs 5 and 6 show negative and positive test outcomes, respectively, the yellow color in 6 indicating the presence of a penicillinase.

Readout/Test Result

Figure 2:
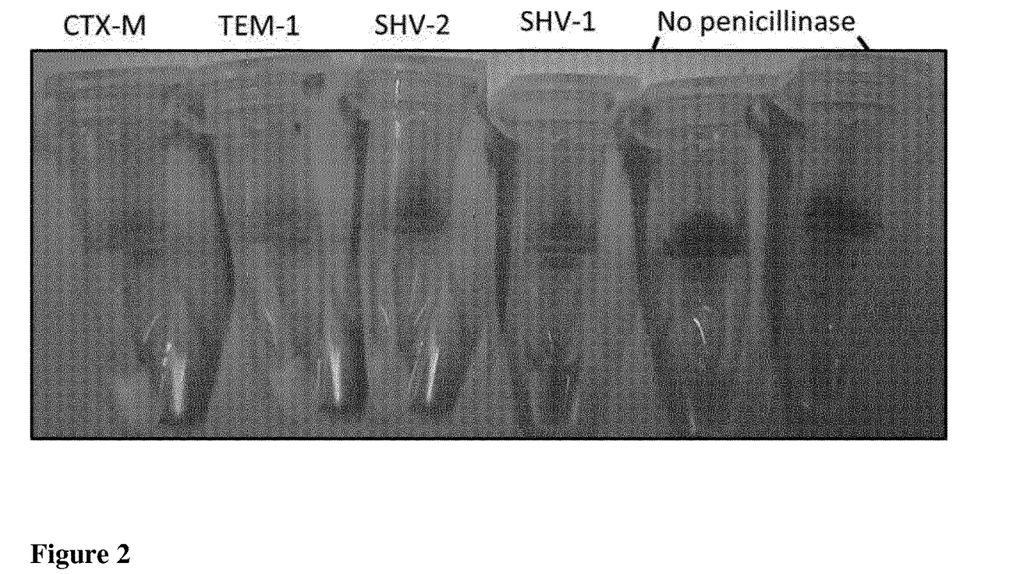
FIG. 2 illustrates an exemplary readout of tests accomplished in accordance with an embodiment, showing exemplary test outcomes.

A change of color of the filter from red to yellow is considered as positive. If there is no change of color, the result can be interpreted as negative. FIG. 2 shows exemplary test outcomes. There are two test tubes with red-colored filters where penicillinase is absent on the right side, and four samples on the left side where the presence of bacteria that are resistant to amoxicillin results in a yellow colored filter.

Example 2

The goal of this example is to demonstrate that the test of the invention is suitable for a rapid determination of the presence of β-lactamase activity in a blood sample.

Test Protocol

Sample preparation: Take 1.5 ml of positive blood culture in a 2 ml Eppendorf tube, add 50 µl of Triton 10% in the tube and incubate 5 min at room temperature and centrifuge 2 min at 20,000×g. Discard supernatant and resuspend the pellet in 500 µl of sterile water or NaCl.

1. Transfer the volume of the prepared sample in a Costar SpinX centrifuge tube and centrifuge 10' at 20,000×g. Discard the supernatant. If there is still liquid above the filter, carefully discard it by inverting the tube.
2. Add 100 µl of B-PER II lysis buffer. Vortex to resuspend the cells.
3. Add 100 µl of solution P on the filter and incubate at 37° C. and notice the color change every 30 min until 90 min Readout/Test Result The test protocol was used for analyzing blood cultures prepared from blood samples characterized previously. The results are shown in Table 1 below.

TABLE 1

Analysis of positive blood culture samples using the kit of the invention.

| Sample | Strain | Gene | 30' | 60' | 90' |
|---|---|---|---|---|---|
| 1 (control) | E. coli | wt | − | − | − |
| 2 | E. coli | TEM-1 | + | + | + |
| 3 | E. coli | TEM-1 | − | − | + |
| 4 | A. baumannii | TEM-1 | + | + | + |
| 5 | A. baumannii | TEM-1 | + | + | + |
| 6 | K. pneumoniae | CTX-M-1 | + | + | + |
| 7 | K. pneumoniae | CTX-M-15 | + | + | + |
| 8 | K. pneumoniae | CTX-M-3 | + | + | + |
| 9 | K. pneumoniae | CTX-M-3 | + | + | + |
| 10 | E. coli | CTX-M-3 | − | + | + |
| 11 | E. coli | CTX-M-3 | + | + | + |

Table 1 shows that after 90 minutes of incubation, positive test outcome was obtained in all samples having β-lactamase activity. Already after 30 minutes of incubation most of the samples having the resistance exhibited a positive test result.

Figure 4:
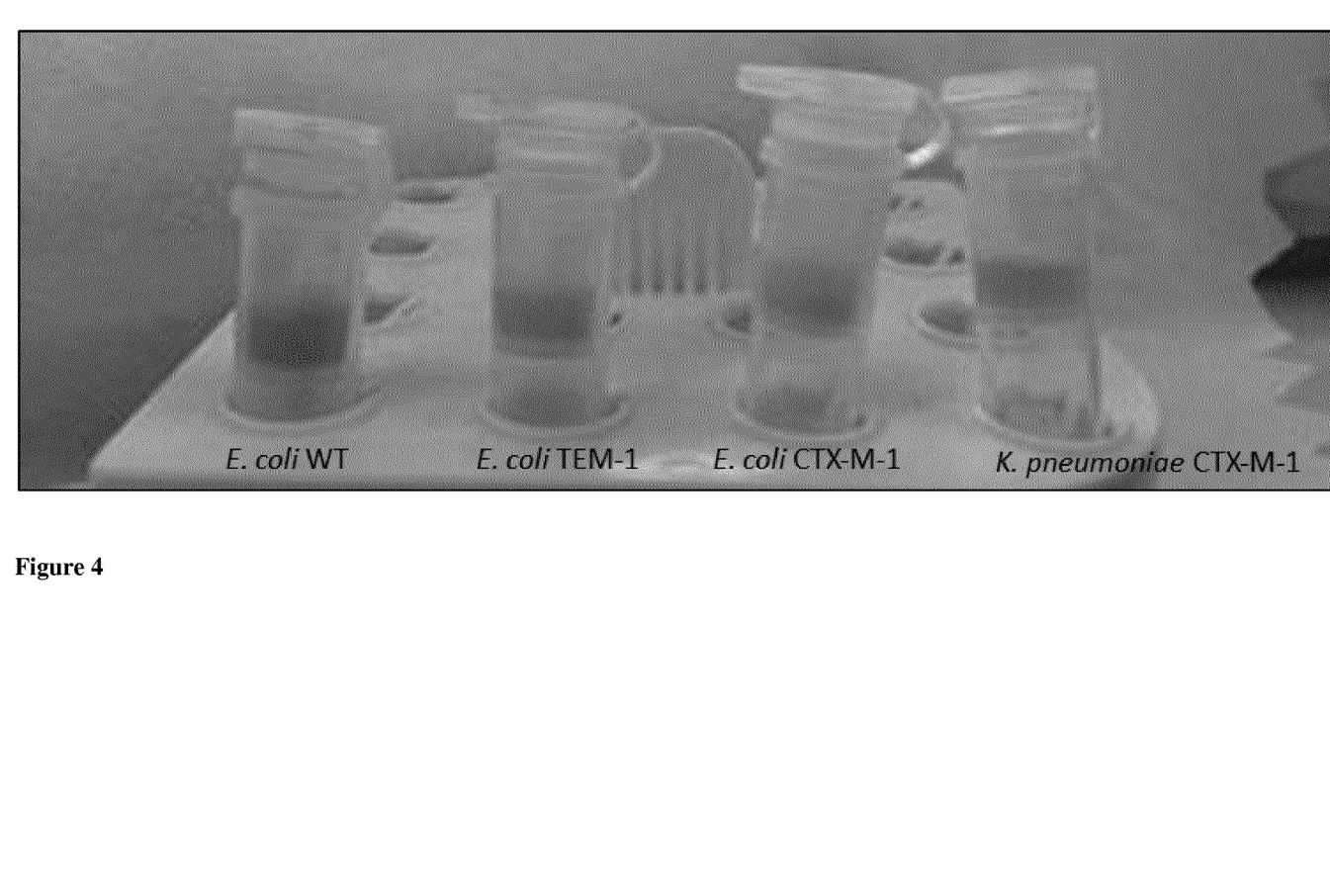
FIG. 4 is a photograph showing an exemplary readout of tests accomplished with blood culture samples, in accordance with an embodiment of the invention.

FIG. 4 shows exemplary test outcomes of the blood test. There is tube on the left side with red-colored sample where penicillinase is absent, and three samples on the right side where the presence of bacteria that are resistant to amoxicillin results in a yellow colored filter.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

The invention claimed is:

1. A method for detecting the presence of a β-lactamase in a sample comprising or derived from a body fluid taken from a patient suffering from an infection, the method comprising:
    providing a filter system comprising a recipient comprising a filter at or in vicinity of the bottom of the recipient, wherein the filter system is adapted to receive said sample and to retain bacteria and/or bacterial proteins contained in the sample, wherein said filter system is adapted to centrifugation;
    providing a tube adapted to centrifugation, said tube being adapted to receive said recipient and to collect a filtrate from said filter system during centrifugation;
    loading the sample onto the recipient comprising said filter;
    centrifuging said filter system comprising said tube, said recipient, and said sample and filtering said sample;
    exposing bacteria in said recipient to a surfactant solution;
    exposing bacterial proteins in said recipient to an indicator solution comprising a color indicator and a β-lactam compound selected from the group consisting of aminopenicillins, natural penicillins, carboxypenicillins and ureidopenicillins; and,
    determining the presence or absence of a β-lactamase from the color of the indicator solution after incubation.

2. The method of claim 1, which comprises:
    (1) providing a filter system comprising a recipient comprising a filter at or in vicinity of the bottom of the recipient, wherein the filter is adapted to receive said sample and to retain bacteria and/or bacterial proteins contained in the sample, wherein said filter system is adapted to centrifugation;
    (2) adding said sample in said recipient of said filter system;
    (3) filtering said sample through said filter for separating bacteria from the sample;
    (4) if not done previously, exposing bacteria to a surfactant solution;
    (5) adding an indicator solution comprising at least one β-lactam compound and a colour indicator into the recipient comprising bacterial proteins;
    (6) incubating the recipient comprising bacterial proteins and said indicator solution;
    (7) determining the presence of a β-lactamase by detecting a color change of said indicator solution, and the absence of a β-lactamase by detecting an absence of a color change of said indicator solution.

3. The method of claim 1, wherein said filter system is a centrifuge tube filter system comprising a filter cup comprising a filter and a centrifuge tube for harbouring said filter cup.

4. The method of claim 1, wherein said color indicator is phenol red.

5. A method for identifying infections treatable with a penicillin compound, the method comprising:
    providing a sample comprising or derived from a body fluid taken from a patient suffering from an infection;
    loading the sample onto a recipient comprising a filter at or in vicinity of the bottom of the recipient, wherein the filter is adapted to receive said sample and to retain bacteria and/or bacterial proteins contained in the sample, wherein said recipient is adapted to centrifugation;

filtering said sample by centrifuging said recipient comprising said filter;

exposing bacteria to a surfactant solution and to a penicillin compound selected from the group consisting of amoxicillin, penicillin G, penicillin P, penicillin V, ampicillin, pivampicillin, hetacillin, bacampicillin, metampicillin, talampicillin, and epicillin;

exposing bacterial proteins in said recipient to an indicator solution comprising a color indicator and a β-lactam compound; and, determining the presence or absence of a β-lactamase from the color of the indicator solution after incubation.

6. The method of claim 5 for identifying urinary tract infections treatable with a penicillin compound wherein said sample is urine sample.

* * * * *